(12) United States Patent
Collazo (10) Patent No.: US 7,033,361 B2
(45) Date of Patent: Apr. 25, 2006

(54) TIBIAL CUTTING GUIDE HAVING VARIABLE ADJUSTMENT

(75) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 54 days.

(21) Appl. No.: 10/782,615

(22) Filed: Feb. 19, 2004

(65) Prior Publication Data

US 2005/0187557 A1    Aug. 25, 2005

(51) Int. Cl.
*A61F 5/00*   (2006.01)
(52) U.S. Cl. .......................................... 606/87; 606/88
(58) Field of Classification Search .. 403/109.1–109.3, 403/109.6, 109.8, 105, 327, 328, 377; 606/86–89; 269/181, 182
See application file for complete search history.

(56) References Cited

U.S. PATENT DOCUMENTS

| | | | |
|---|---|---|---|
| 3,599,960 A * | 8/1971 | Phillips | 269/182 |
| 3,749,088 A * | 7/1973 | Kohlmann | 600/215 |
| 4,524,766 A | 6/1985 | Petersen | |
| 4,736,737 A | 4/1988 | Fargie et al. | |
| 4,759,350 A | 7/1988 | Dunn et al. | |
| 4,841,975 A | 6/1989 | Woolson | |
| 5,002,547 A | 3/1991 | Poggie et al. | |
| 5,228,459 A | 7/1993 | Caspari et al. | |
| 5,304,181 A * | 4/1994 | Caspari et al. | 606/80 |
| 5,445,640 A | 8/1995 | Johnson et al. | |
| 5,897,109 A * | 4/1999 | Lin | 269/182 |
| 5,976,145 A * | 11/1999 | Kennefick, III | 606/80 |
| 6,017,306 A * | 1/2000 | Bigliani et al. | 600/234 |
| 6,090,114 A * | 7/2000 | Matsuno et al. | 606/88 |

* cited by examiner

Primary Examiner—David O. Reip
Assistant Examiner—Richard Shaffer
(74) Attorney, Agent, or Firm—Lerner, David, Littenberg, Krumholz & Mentlik, LLP (57) ABSTRACT

A method and a device for positioning a cutting guide for cutting a bone such as the tibia has a first elongated member having a longitudinally extended threaded surface. A second member is provided for receiving the first member. The second member includes an adjustment element mounted for rotation on the second member and for movement transverse to a longitudinal axis of the first member. The adjustment element has a threaded surface selectively engageable with the first member threaded surface. A biasing element extends between the second member and the adjustment element for biasing the adjustment element into engagement with the threaded outer surface of the first member so that rotation of the adjustment element causes relative movement between the first and second members. The adjustment element is moveable against the biasing element in the transverse direction out of engagement with the first member. Thus, the device allows both free sliding and threaded adjustment along the axis.

12 Claims, 6 Drawing Sheets

TIBIAL CUTTING GUIDE HAVING VARIABLE ADJUSTMENT

BACKGROUND OF THE INVENTION

This invention relates to a bone resection guide for use in orthopedic surgery. More particularly, this invention relates to a tibial resection guide and a mechanism for allowing both coarse and fine adjustment of the resection guide without requiring repositioning of the surgeon's hand and without requiring any tightening of a locking knob to lock a pair of telescoping rods in place.

In total knee arthroplasty, particularly in the resection of the distal femur and proximal tibia, cutting blocks are positioned in close proximity to the bone and adjusted in either a proximal or distal direction to achieve a measured amount of resection determined by the surgeon. Once the cutting block is set in the desired resection level, it is locked in place to prevent movement during the cutting of the bone. Three methods of adjustment and locking are currently employed in achieving this surgical step.

In a first method, the height of resection is achieved by moving a telescoping rod which, itself, is attached to the cutting block in either a proximal or distal direction and subsequently locking it at a desired position by turning a threaded knob mounted in the outer tubular rod into engagement with an inner rod. A drawback of this method is that it does not provide a fine adjustment of the cutting block which is counted in millimeters and the position of the cutting block may slip, since the degree of locking is dependent on how tight the surgeon turns the thumbscrew. Some designs utilize a camlock mounted between the inner and outer telescoping portions to more Positively lock the rods together. Woolson U.S. Pat. No. 4,841,975 discloses a tibial resector guide having a telescoping rod carrying a cutting head at its upper end. The cutting guide is adjustable relative to the telescoping rod by a pair of oppositely positioned thumbscrews. The guide may be aligned with the mechanical axis of the joint by using a slidable plate.

Poggie et al. U.S. Pat. No. 5,002,547 and Petersen U.S. Pat. No. 4,524,766 disclose tibial resector guides wherein the cutting guides are fixed to a telescoping rod.

Dunn et al. U.S. Pat. No. 4,759,350 discloses a tibial resector guide having a fixed head carried by a telescoping rod. A separate pinning strap is carried by the rod adjacent the head. The strap is fixed to the telescoping rod.

Fargie et al. U.S. Pat. No. 4,736,737 discloses a tibial resector head connected to an intramedullary rod and shiftable in the longitudinal direction only.

U.S. Pat. No. 5,228,459 to Caspari et al. relates to a tibial resection guide having both a telescoping adjustment and a threaded adjustment.

U.S. Pat. No. 5,445,640 to Johnson et al. relates to a tibial resection guide which includes a thumbwheel for locking the telescoping rods in position and includes a length adjustment mechanism which provides small adjustments in the overall length of the tibial resector guide.

SUMMARY OF THE INVENTION

It is one object of the invention to provide a simplified apparatus for adjusting a resection guide so that a cutting surface can be properly positioned with respect to a bone.

It is yet another object of the invention to provide an apparatus in which the surgeon can single handedly adjust the position of the cutting guide in both a coarse and fine adjustment.

It is yet another object of the invention to provide a connection between two telescoping parts, which connection can selectively allow relative sliding between the parts or a threaded adjustment between the parts.

These and other objects of the invention are provided by a device having both a free sliding and a threaded adjustment. The device includes an assembly with a first member having at least a partially threaded outer surface and a second member having an inner surface, the first member having a longitudinally extended threaded outer surface received within the inner surface of the second member. The first member may be a threaded rod. An adjustment element having an opening for receiving the first member is mounted on the second member. The adjustment element may be in the form of a ring with a knurled outer surface and a threaded inner bore. The inner bore of the adjustment element is larger than the cross-section of the first member. Preferably, the adjustment element is mounted on the second member for rotation with respect to both the first and second members. The threaded opening of the adjustment element is selectively engageable with the first member threaded surface upon movement of the adjustment element in a direction transverse to the longitudinal axis of the first member of the assembly. The first and second members may be a telescoping assembly.

A biasing element extends between the second member and the adjustment element for biasing the adjustment element into engagement with the threaded outer surface of the first member. When this occurs, rotation of the ring-shaped adjustment element permits the threaded adjustment of the telescoping assembly. The adjustment element is moveable against this spring in the transverse direction out of threaded engagement with the first member to permit free sliding adjustment of the telescoping assembly. Release of the adjustment element results in engagement of the threads and a locking of the assembly. A cutting block, such as a tibial plateau resection guide, may be mounted on the first member or alternatively, may be mounted on the second member. When mounted on the second member, the guide can then be moved in the proximal-distal direction with respect to the first member. The second member includes mounts for the springs which act to bias the adjustment element which, preferably, may be coil springs or leaf springs. Preferably, these springs engage a bushing block attached to the adjustment element mounted for a transverse movement with respect to the second member against the spring force with threaded inner bore of the adjustment element selectively moving into and out of engagement with the threaded surface of the first member. The first member may be polygonal in cross-section and preferably has threads on only one side thereof. The second member may be clamped with respect to the patient's ankle in any known manner as described in the prior art set forth above.

The invention also relates to a method for locating a tibial cutting guide block with respect to the proximal tibia which includes mounting on the lower leg an adjustment device having first and second telescoping members. One of the first or second members has the cutting block fixedly mounted thereon, which member is slidably mounted on the other member for movement in a proximal-distal direction along a longitudinal axis. The surgeon slides one member with respect to the other member to coarsely set the location of the cutting block. The surgeon does this by moving an adjustment element rotatably mounted between the first and second members in a direction transverse to the proximal-distal longitudinal axis. The adjustment element has a threaded surface for engaging the mating threaded surface on one of the first or second members. The adjustment element is spring biased into engagement with the threaded surface. The sliding between the first and second members is permitted for coarse adjustment by moving the adjustment element in the transverse direction against the spring bias so that the threads disengage. The cutting block may be adjusted in finer or smaller increments by rotating the adjustment element while the threads on the threaded surface of the adjustment element are in engagement with the threads on the one of the first and second members. This is permitted when the surgeon releases the adjustment element and it springs back into the engaged position.

In a preferred embodiment, the adjustment element is a wheel having a knurled or ribbed outer surface and an inner bore having two diameters preferably defining a step therebetween. The smallest diameter is threaded and the larger diameter has a smooth surface to accept a bushing around which the adjustment wheel may rotate. In the preferred embodiment, the bushing is integral with a moveable guide block. The adjustment wheel, guide block and bushing have an internal opening through which the threaded first member extends. The guide block includes one or a pair of rails which engage the grooves in the second member which act to ensure that the guide block moves in a transverse direction when the adjustment element is depressed.

The guide block has a cylindrical bushing portion with an outer surface which engages the larger inner surface of the adjustment wheel so that the adjustment wheel may be rotated about the guide block bushing outer surface. The biasing elements or springs act against the adjustment wheel guide block which is guided by a rail or rails thereon when the surgeon depresses the adjustment wheel to disengage the threads thereof from the threaded member or rod. If coil springs are used, both the first member and the guide block may include cylindrical recesses to capture the respective ends of the coil springs. In the preferred embodiment, the second member includes the cutting block and has tracks or grooves for engaging the rails of the wheel guide block to ensure movement thereof in a direction perpendicular to the longitudinal axis of the second member.

DETAILED DESCRIPTION

Figure 1:
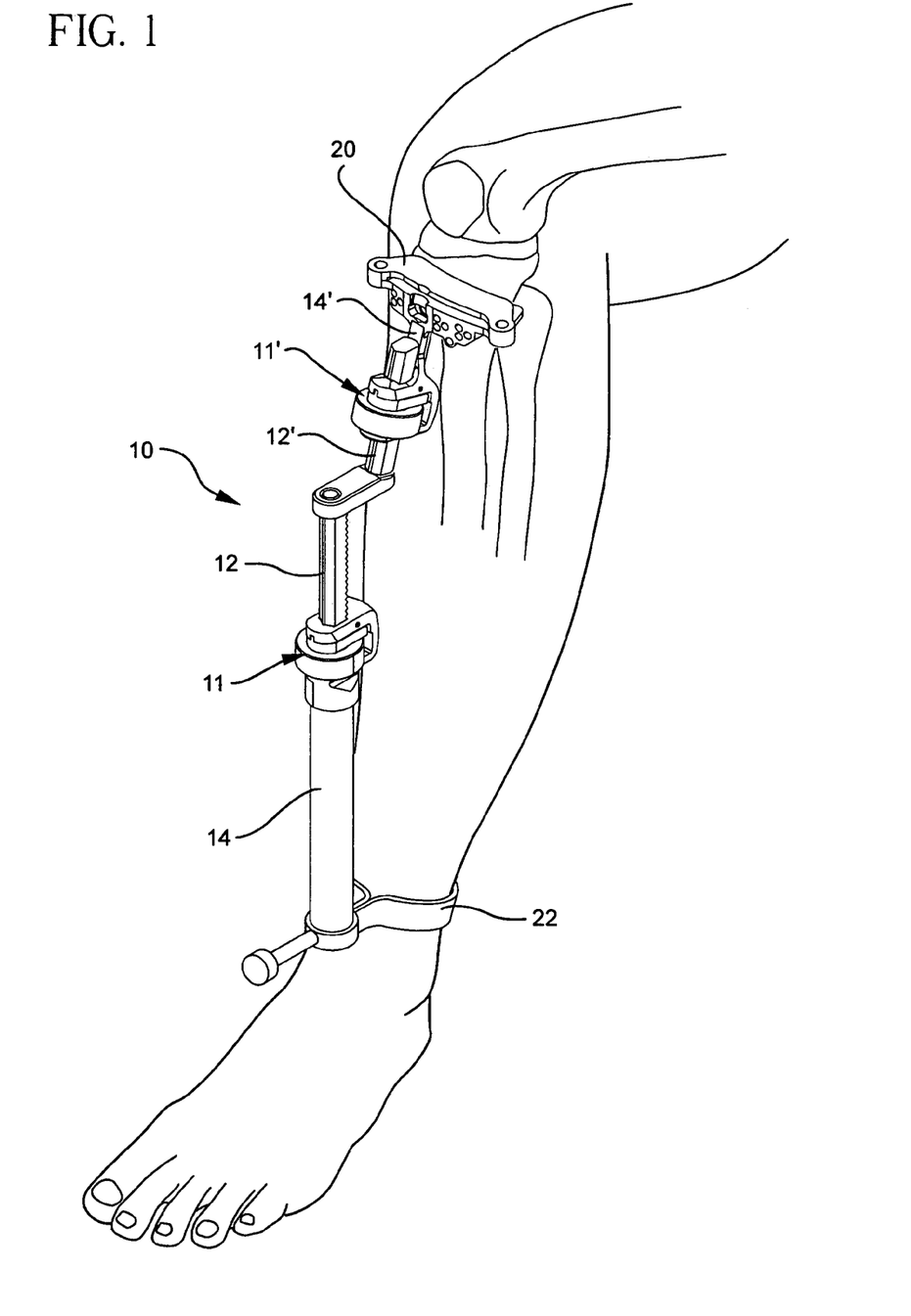
FIG. 1 is an isometric view of the tibial cutting guide of the present invention mounted on a patient's lower leg.
Figure 2:
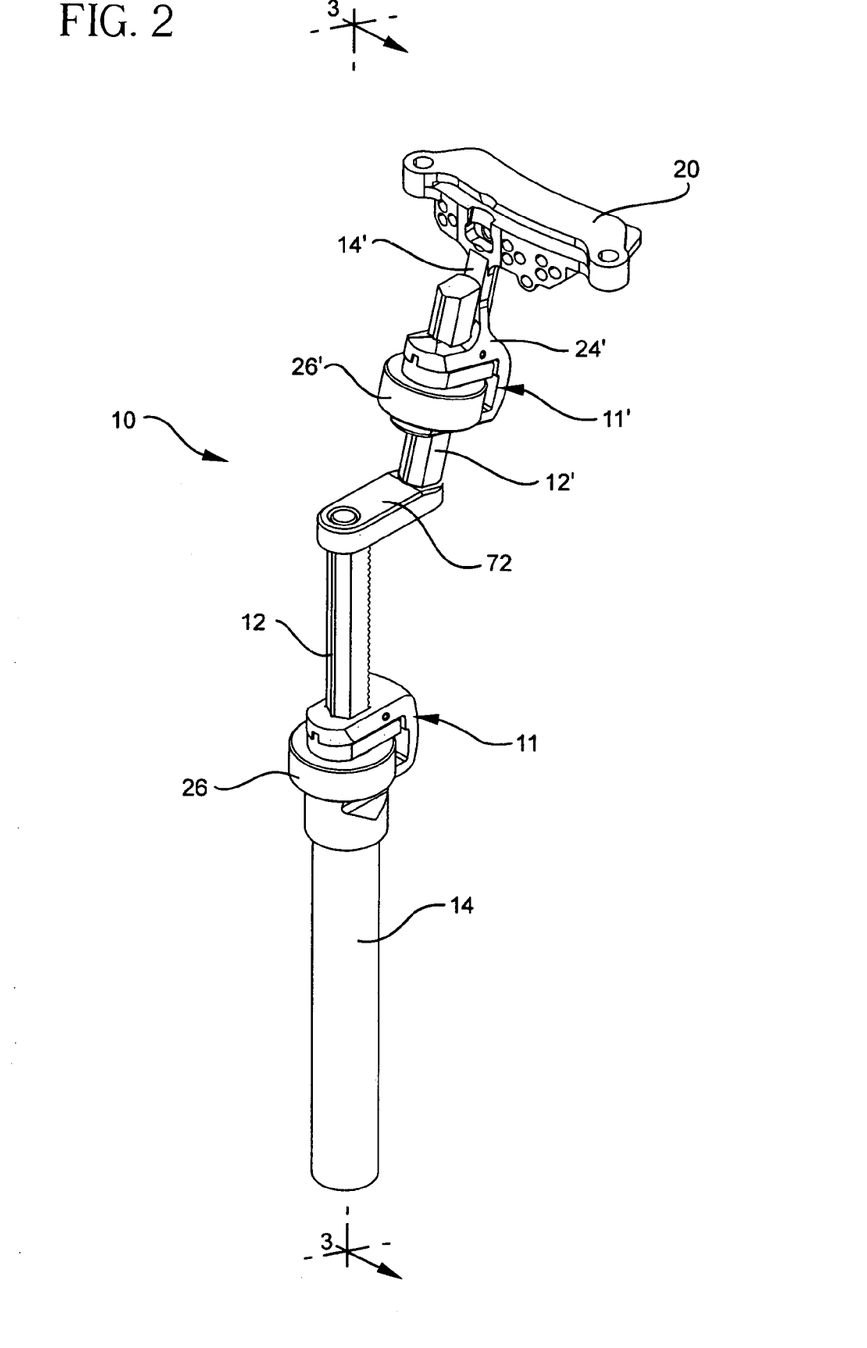
FIG. 2 is a view of the tibial cutting guide of FIG. 1 shown removed from the tibia.
Figure 3:
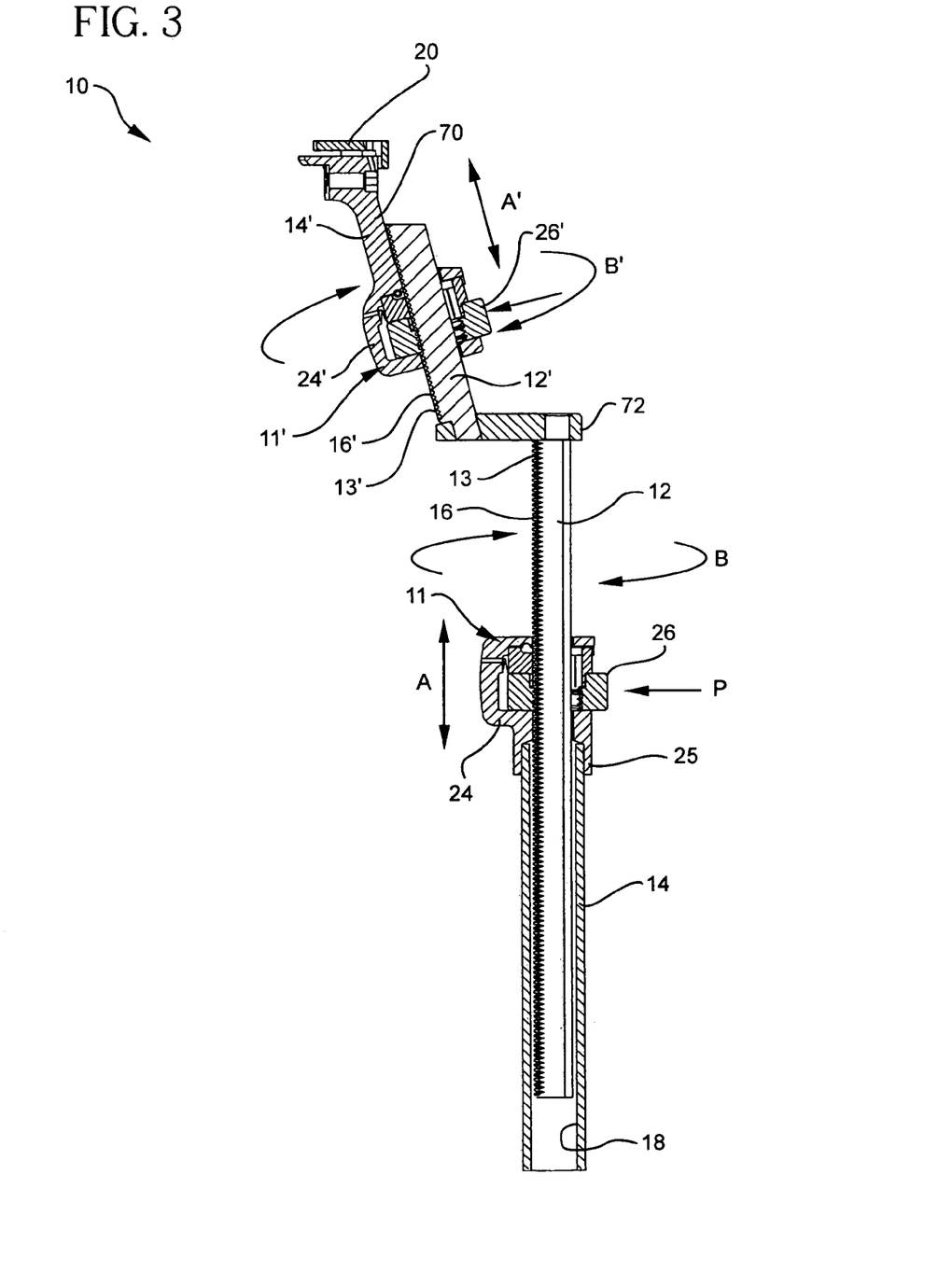
FIG. 3 is a cross-sectional view of the tibial cutting guide of FIG. 2 along lines 3—3.

Referring to FIGS. 1 and 2, there is shown a tibial cutting guide including the adjustment mechanism of the present invention generally denoted as 10 mounted on the lower leg of a patent. In the preferred embodiment, the cutting guide 10 includes a pair of adjustment mechanisms 11, 11' with each adjustment mechanism 11, 11' being structurally the same. Adjustment mechanism 11' is optional and can be eliminated if adjustment using mechanism 11 provides sufficient adjustability. Guide 10 and adjustment mechanism 11 include a pair of telescoping parts 12, 12' and 14, 14'. In the preferred embodiment as best shown in FIG. 3, parts 12, 12' are solid rods with one side surface 13 thereof having threads or partial threads 16 whose function will be discussed below parts 12, 12' are connected by member 72 in the preferred embodiments. In the preferred embodiment, part 14 is a hollow tubular member which telescopically receives rod 12 in an inner generally cylindrical bore 18 thereof.

In the preferred embodiment, adjustment mechanism 11' has a threaded rod 12' with part 14' being integral with cutting block 20 and receiver part 24' of adjustment mechanism 11'.

In the preferred embodiment, the proximal end of the adjustment mechanism 11' includes a tibial resection block 20 for the resection of the proximal tibia. Cutting block 20 can be of any design and in what manner it allows the resection of the proximal tibia is not material to the invention herein. Likewise, the distal portion of the adjustment mechanism in the preferred embodiment includes a ankle clamp 22 which is mounted to part 14. The design of the ankle clamp is not critical to the invention.

Figure 6:
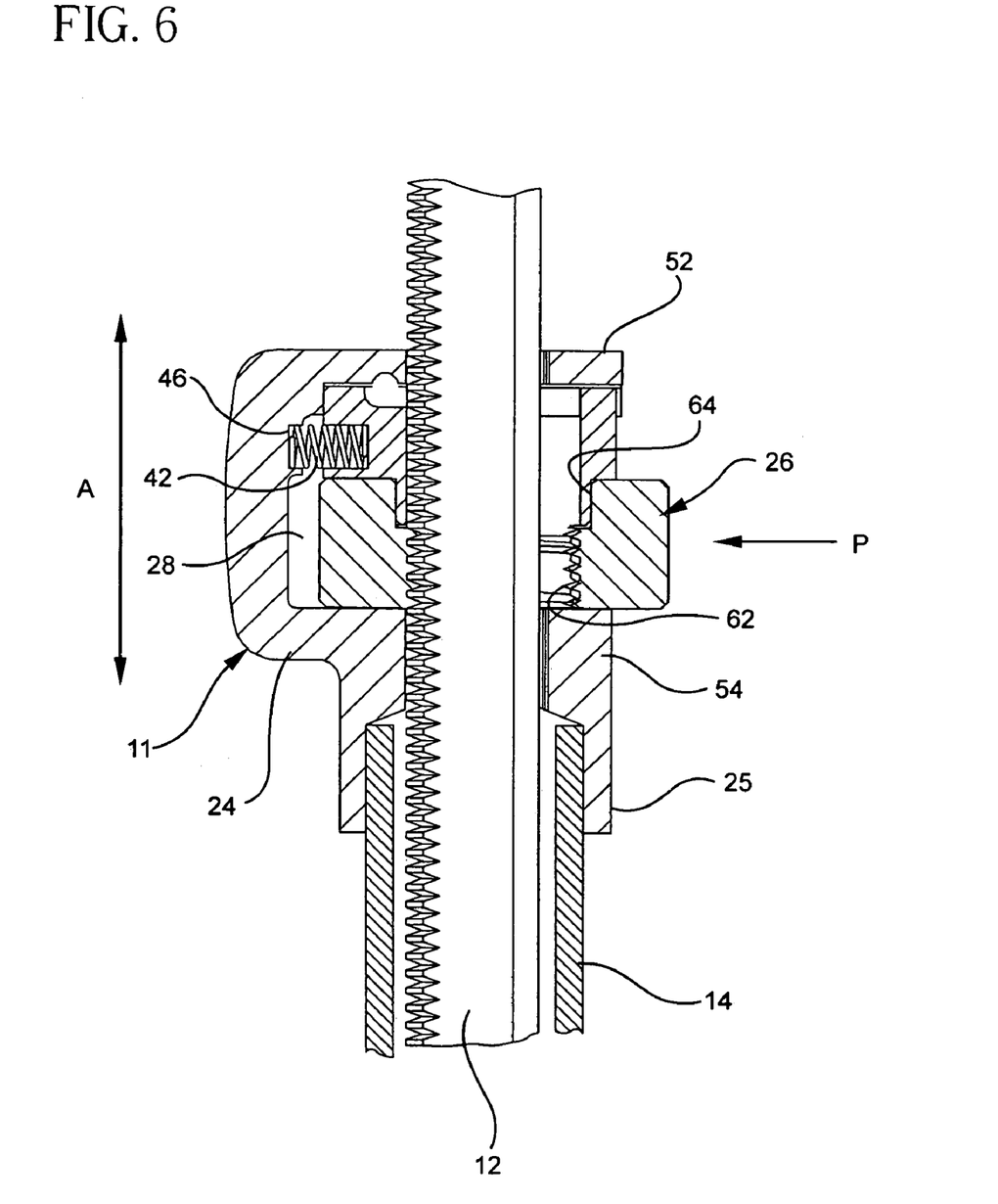
FIG. 6 is an enlarged cross-sectional view of the assembled adjustment mechanism of the present invention.

In the preferred embodiment, a receiver part 24 is mounted on the proximal end of part 14 and the distal end of part 14' and is either formed integrally therewith or fixedly attached to the end thereof. As shown in FIG. 6, the preferred method of attachment of receiving part 24 to part 14 is by welding a tubular female portion 25 of part 24 onto a proximal male tubular end of part 14. Alternately, the tubular end of part 14 could be threaded into portion 25.

Referring to FIGS. 2 through 6, an adjustment wheel 26, 26' is shown to be slidably mounted within a recessed portion 28 of receiver part 24, 24', respectively. In the preferred embodiment, adjustment wheel 26 is rotatably mounted on a guide block 30 and has a knurled or rubber outer surface 60 and a threaded inner bore 62. The preferred guide block 30 includes one or a pair of rails 32 slidably mounted in one or a pair of grooves 34 formed on an inner surface 35 of receiving part 24, 24'. Guide block 30 includes a throughbore 36 through which threaded rod 12 passes and includes a bushing extension 31 on which wheel 26, 26' rotates. In the preferred embodiment, bore 36 has a larger cross-section than does rod 12, 12'. Guide block 30, in the preferred embodiment, includes a pair of cylindrical bores 38, 40 which receive a pair of coil springs 42, 44, respectively. The ends of springs 42, 44 opposite guide block 30 are received in a pair of cylindrical recesses 46, 48 formed on the inner side of end wall 50 located at the base of recess 28 of receiving part 24, 24'. Thus, guide block 30 is biased by springs 42, 44 away from end wall 50. By compressing springs 42, 44, guide block 30 can be moved inwardly towards wall 50 with respect to recessed portion 28 in part 24, 24'. This is permitted by the fact that bore 36 is larger that the cross-section of rod 12, 12'.

In the preferred embodiment, receiving part 24, 24' includes an upper wall 52 and a lower wall 54 separated by wall 50, each having a through opening 56 for slidingly receiving rod 12, 12'. In the preferred embodiment, openings 56 in walls 52, 54 have the same cross-sectional shape as the rod 12, 12' and are designed to closely receive and guide the rod 12, 12'.

Figure 4:
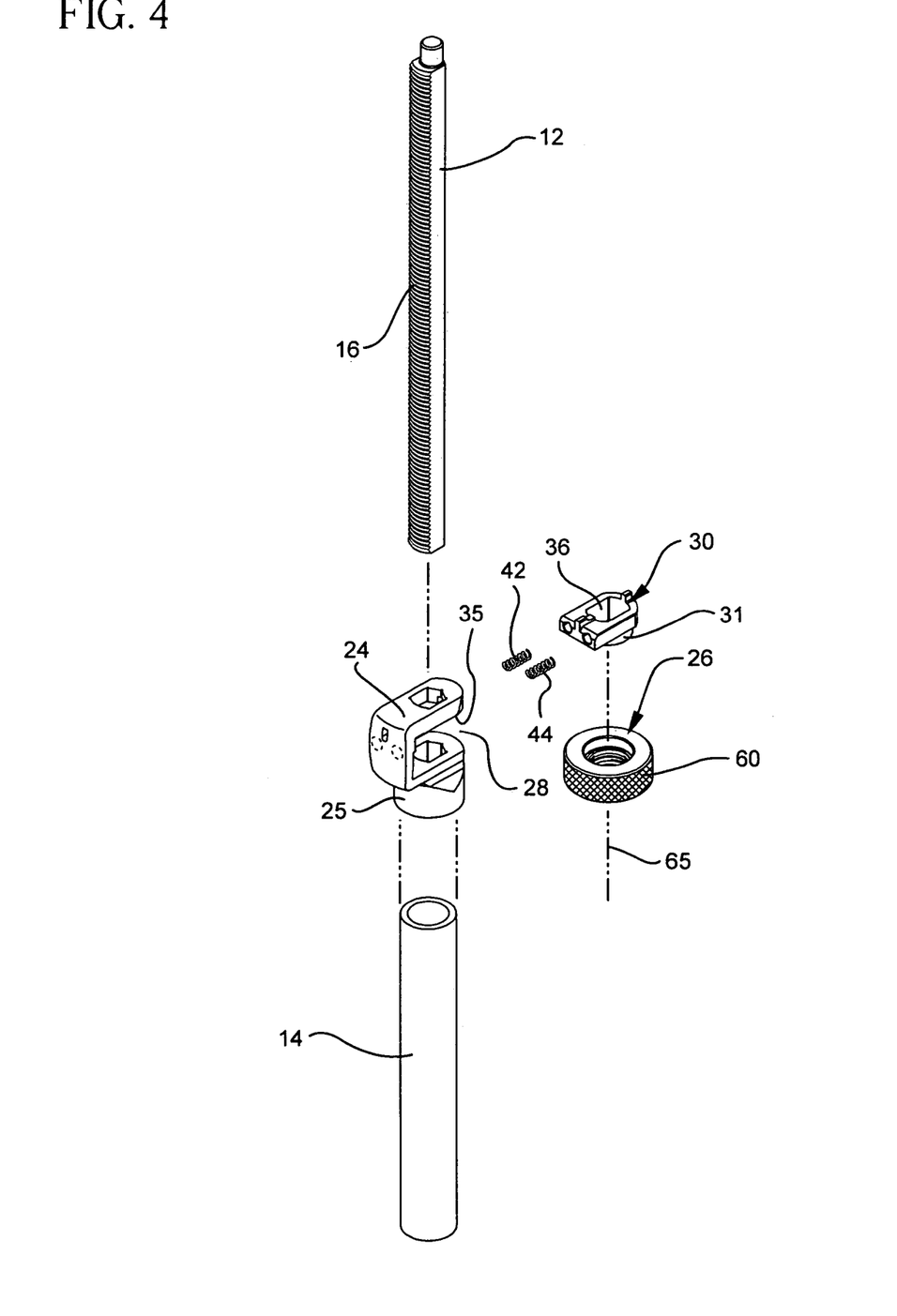
FIG. 4 is an exploded view of the variable adjustment mechanism of the tibial cutting guide shown in FIGS. 1–3.
Figure 5:
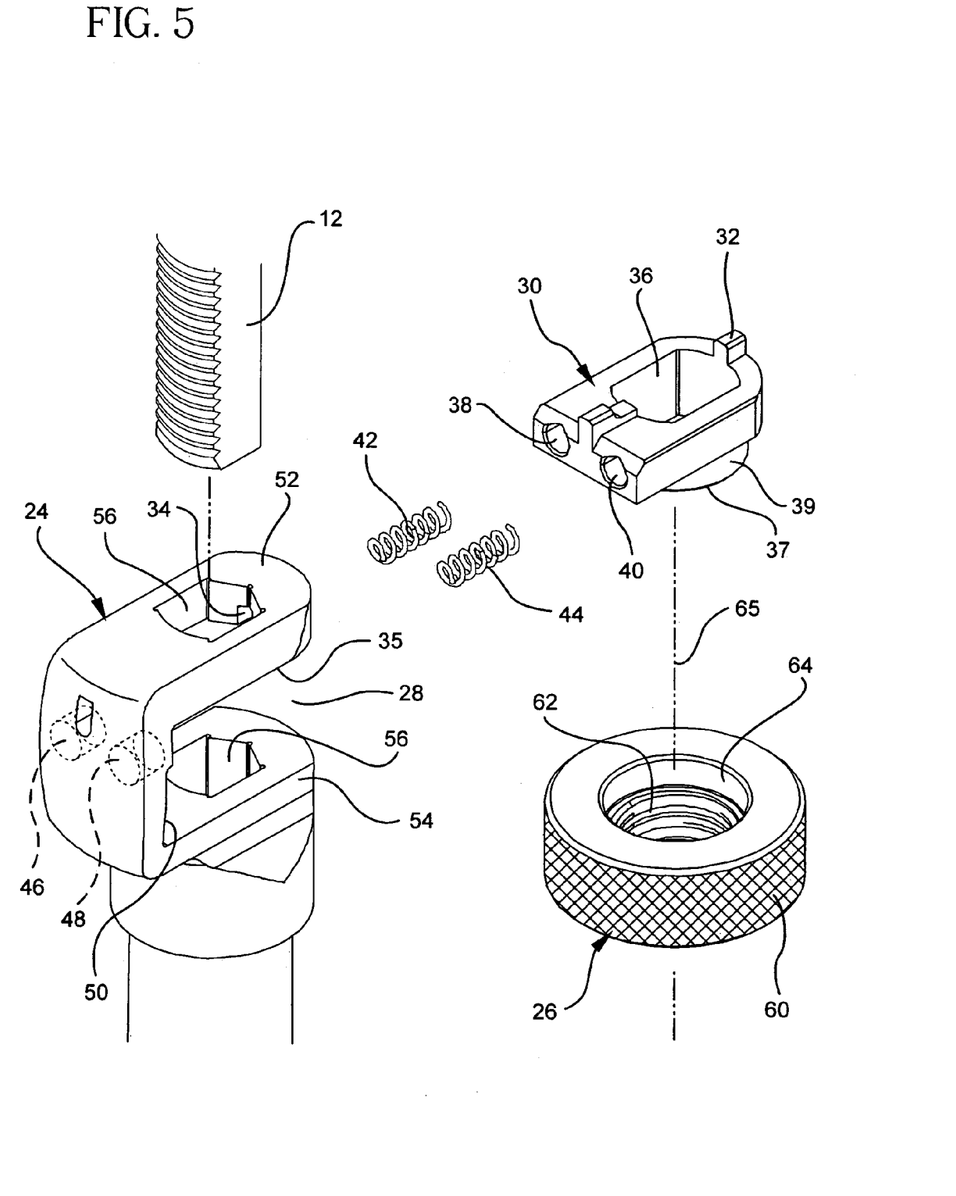
FIG. 5 is an enlarged view of the adjustment mechanism shown in FIG. 4.

Referring to FIGS. 4 and 5, there is shown adjustment wheel 26, 26' which has a circular outer diameter 60 which may be knurled or otherwise roughened to make it easier to rotate by hand. The inner bore of wheel 26, 26' has two spaced portions, a threaded portion 62 and a non-threaded portion 64, aligned along the axis 65 of the inner bore of wheel 26. Non-threaded portion 64 rotatably receives bushing extension 31 of guide block 30. In the preferred embodiment, the central axis of circular bushing 37 is, upon assembly into the bore of adjustment wheel 26, 26' co-axial with axis 65. Once assembled, adjustment wheel 26 and guide block 30 slide within opening 28 as a unit.

The cylindrical outer surface 39 of extension 37 acts as a bushing on which the inner portion 64 of adjustment wheel 26 rotates. During assembly, adjustment wheel 60 is mounted on guide block 30 which, in turn, is mounted within recess 28 of receiving part 24, 24'. Partially threaded rod 12, 12' is then inserted through receiving part 24, 24' and guide block 30 with the adjustment wheel 26 mounted thereon.

The threaded inner bore 62 of wheel 26 is biased by coil springs 42, 44 into engagement with threaded surface 13 of rod 12. Engagement between the threads 16 on rod 12, 12' and the threaded inner bore portion 62 locks the relative axial movement between rod 12, 12' and part 14, 14'. However, rotation of adjustment wheel 26 while engaged with threads 16 causes movement between parts 12 and 14. Thus, for a small or fine adjustment the rotation of wheel 26, 26' in one direction causes the rod 12, 12' to move upwardly with respect to part 14, 14' and rotation in the opposite direction makes the rod 12, 12' move downwardly with respect to part 14, 14'. The fineness of this threaded adjustment is determined by the pitch of the threads 16 on rod 12, 12' and inner bore 62 of wheel 26, 26'. If a coarse adjustment between rod 12, 12' and part 14, 14' is desired, pressure on surface 60 of wheel 26, 26' in a direction of the arrows on FIGS. 3 and 6 compressing the springs 42, 44 disengages threads 62 from threads 16 of rod 12, 12' and allows unrestricted sliding motion between rod 12, 12' and part 14, 14'. Obviously, for this to be accomplished, the diameter of the threaded bore portion 62 must be greater than the cross-section of the rod 12, 12' so that sufficient radial movement is allowed for the thread 62 to disengage from the threads 16. Release of guide block 30 allows springs 42, 44 to re-expand radially which results in the reengagement the threads 62 and 16. This locks the axial movement between rod 12, 12' and part 14, 14' and permits the fine adjustment by rotation of wheel 26, 26'.

Referring again to FIGS. 1–3, there is shown second adjustment mechanism 11' which may optionally be used. Adjustment mechanism 11' is identical in function to cutting block 11 in that it includes an adjustment wheel 26' received within a receiving part 24' which are identical in design to wheel 26 and receiving part 24 with the exception that instead of a female tubular part 25, receiving part 24' is attached to or integral with a solid arm 70 which forms telescopic part 14'. Arm 70 includes cutting block 20 either integral therewith or fixedly attached thereto by any convenient means. Part 12' includes surface 13' which includes teeth 16' and functions identically to part 12 discussed above.

Both adjustment mechanisms 11, 11' allow proximal-distal movement in the direction of arrows A and A', respectively. Part 12' can be inclined towards the tibia with respect to axis of part 12 so that proximal-distal movement of parts 12' and 14' move the cutting block 20 in an anterior-posterior direction.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention of claimed is:

1. A device for positioning a cutting guide for a bone, the device having both free sliding and threaded adjustment along an axis comprising:
   a first elongated member having a longitudinally extending threaded outer surface;
   a second member for receiving said first member having an adjustment element mounted for rotation thereon and for movement transverse to a longitudinal axis of said first member, said adjustment element having a threaded surface selectively engageable with said first member threaded surface; and
   a biasing element extending between said second member and said adjustment element for biasing said adjustment element into engagement with said threaded outer surface of said first member so that rotation of said adjustment element causes relative movement between said first and second members, said adjustment element moveable against said biasing element in said transverse direction out of engagement with said first member.

2. The device as set forth in claim 1 wherein said second member has a bore therethrough to slidably receive said first member.

3. The device as set forth in claim 2 wherein said bore and said first member have complimentary non-circular cross-sections.

4. The device as set forth in claim 1 wherein said adjustment element is a wheel having an inner bore with a threaded portion.

5. The device as set forth in claim 4 wherein said adjustment element inner bore has a non-threaded portion having a diameter larger than said threaded portion.

6. The device as set forth in claim 5 further comprising a guide block having a bushing portion rotatably mounted within said non-threaded bore portion of said adjustment element and a guide portion slidably mounted on said second member for movement in said directions transverse to said longitudinal axis.

7. The device as set forth in claim 6 wherein said guide portion includes said biasing element.

8. The device as set forth in claim 7 wherein said guide portion has at least one rail for slidably engaging groove in said second member.

9. The device as set forth in claim 6 wherein said guide portion includes an internal opening for receiving said first member.

10. The device as set forth in claim 1 wherein said bone cutting guide is a tibial resection guide.

11. The device as set forth in claim 10 wherein one of said first and second members includes an ankle clamp.

12. The device as set forth in claim 1 wherein said first member is telescopingly receiving within a bore in said second member.

* * * * *

UNITED STATES PATENT AND TRADEMARK OFFICE
CERTIFICATE OF CORRECTION

PATENT NO. : 7,033,361 B2
APPLICATION NO. : 10/782615
DATED : April 25, 2006
INVENTOR(S) : Carlos E. Collazo It is certified that error appears in the above-identified patent and that said Letters Patent is hereby corrected as shown below:

Column 1, line 33, "Positively" should read --positively--.
Column 4, line 5, "below parts" should read --below. Parts--.
Column 4, line 6, "embodiments" should read --embodiment--.

Signed and Sealed this

Fifteenth Day of August, 2006

JON W. DUDAS
*Director of the United States Patent and Trademark Office*